United States Patent [19]

Siskin et al.

[11] 4,025,577

[45] May 24, 1977

[54] HYDROALKYLATION OF PARAFFINS WITH OLEFINS UTILIZING HYDROGEN FLUORIDE AND METAL PENTAFLUORIDE CATALYST

[75] Inventors: Michael Siskin, Maplewood; Joseph J. Porcelli, Scotch Plains, both of N.J.

[73] Assignee: Exxon Research and Engineering Company, Linden, N.J.

[22] Filed: June 12, 1975

[21] Appl. No.: 586,176

[52] U.S. Cl. .................. 260/683.51; 260/683.47
[51] Int. Cl.² ..................................... C07C 3/54
[58] Field of Search ............... 260/683.51, 683.53, 260/683.47, 683.44, 683.58

[56] References Cited

UNITED STATES PATENTS

| | | | |
|---|---|---|---|
| 2,355,339 | 8/1944 | Story | 260/683.53 |
| 2,406,954 | 9/1946 | Linn | 260/683.51 |
| 3,201,494 | 8/1965 | Oelderik et al. | 260/683.51 |
| 3,678,120 | 7/1972 | Bloch | 260/683.47 |
| 3,852,371 | 12/1974 | Kemp | 260/683.47 |

*Primary Examiner*—George Crasanakis
*Attorney, Agent, or Firm*—John W. Ditsler

[57] ABSTRACT

High octane alkylates are prepared by selectively alkylating paraffinic hydrocarbons with a hydrocarbon selected from the group consisting of paraffins and olefins at alkylation conditions in the presence of hydrogen and of a catalyst comprising (a) one or more Lewis acids of the formula $MX_n$ where M is selected from the Group IIIA, IVB, V or VIB elements of the Periodic Table, X is a halogen, $n$ is the ratio of halogen atoms to atoms of M and varies from 1–8, and (b) a hydrogen halide.

15 Claims, No Drawings

HYDROALKYLATION OF PARAFFINS WITH OLEFINS UTILIZING HYDROGEN FLUORIDE AND METAL PENTAFLUORIDE CATALYST

BACKGROUND OF THE INVENTION

The present invention relates to a process for the selective hydroalkylation of paraffinic hydrocarbons with a hydrocarbon selected from the group consisting of paraffins and olefins in the presence of a catalyst comprising (a) one or more Lewis acids of the formula $MX_n$, where M is selected from Group IIIA, IVB, V or VIB elements of the Periodic Table, X is a halogen, $n$ is the ratio of halogen atoms to atoms of M and varies from 1–8, and (b) a hydrogen halide. The preferred Lewis acid is a metal halide, preferably tantalum pentafluoride, niobium pentafluoride or mixtures thereof. The preferred hydrogen halide is hydrogen fluoride.

DESCRIPTION OF THE PRIOR ART

The acid catalyzed addition of an alkane to another alkane or an alkene is well known in the art. Generally, the catalytic alkylation of paraffins involves the addition of an alkyl cation derived from an isoparaffin containing a tertiary hydrogen to an olefin. The process is used by the petroleum industry to prepared highly branched $C_6$–$C_9$ paraffins that are high quality fuels for internal combustion and other engines. The process conditions required and the product composition depend on the particular hydrocarbons involved in the reaction.

Hydrocarbon conversion processes involving the use of metal halide based catalysts have been extensively described in the prior art. For example, U.S. Pat. Nos. 2,683,763 and 2,683,764 disclose the tantalum pentafluoride or columbium (niobium) pentafluoride in combination with hydrogen fluoride can be used to refine hydrocarbon oils or to promote the disproportionation of alkyl-substituted aromatic materials. The patentees also disclose that hydrogen fluoride/tantalum pentafluoride and hydrogen fluoride/columbium pentafluoride are powerful catalysts for isomerization, alkylation, cracking and other reactions of aromatics. More recently, U.S. Pat. No. 3,708,553 teaches that high octane alkylates can be produced by contacting paraffinic and/or alkyl substituted aromatic hydrocarbons with olefins in the presence of a catlyst comprising one or more metal halides and a strong Bronsted acid selected from the group consisting of fluorosulfuric acid and trifluoromethane sulfonic acid and mixtures thereof. However, when paraffinic hydrocarbons are selectively alkylated with another paraffin or an olefin in the presence of hydrogen using the catalyst system of the present invention as described hereinafter, there will result an alkylate of enhanced product quality because of better selectivity to desired alkylate products than that obtained using catalyst systems taught in the prior art.

SUMMARY OF THE INVENTION

Now in accordance with the present invention, it has been discovered that i-$C_4$–$C_{12}$ paraffinic hydrocarbons are selectively alkylated with a hydrocarbon selected from the group consisting of paraffins and olefins at alkylation conditions in the presence of hydrogen and of a catalyst comprising (a) a first component, one or more Lewis acids of the formula $MX_n$ where M is selected from the Group IIIA, IVB, V or VIB elements of the Periodic Table, X is a halogen, preferably fluorine, $n$ is the ratio of halogen atoms to atoms of M and varies from 1–8, and (b) a second component, a hydrogen halide. In general, reaction temperatures may range broadly, i.e. from about −100° to about +100° C, preferably from about −30° to about +75° C, and more preferably from about −10° to about +60° C.

Catalysts of the type described herein have been well known to catalyze alkylation reactions, particularly where the second component is fluorosulfuric acid or trifluoromethanesulfonic acid. It has been surprisingly found, however, that when a hydrogen halide, preferably hydrogen fluoride, is employed in conjunction with hydrogen and a metal halide, preferably tantalum pentafluoride, niobium pentafluoride and mixtures thereof, the reaction is highly selective to the formation of desirable alkylate products. Thus, according to the present invention, selectivity to $C_6$–$C_{12}$ branched alkylate product is enhanced because the formation of intermediate esters and subsequent polymerization reactions which occur when using either fluorosulfuric acid or trifluoromethanesulfonic acid under similar reaction conditions is minimized. Preferably, the present alkylation process is conducted in the substantial absence of aromatic compounds.

DETAILED DESCRIPTION OF THE INVENTION

The hydrocarbon conversion catalyst referred to herein comprises one or more Lewis acids of the formula $MX_n$ where M is selected from the Group IIIA, IVB, V or VIB elements of the Periodic Table or their mixtures, X is a halogen, preferably fluorine, $n$ is the ratio of halogen atoms to atoms of M and varies from 1–8, and (b) a hydrogen halide. The Periodic Table referred to is that described in "The Encyclopedia of Chemistry", Reinhold Publishing Corporation, 2nd Ed. (1966) at page 790. The term "elements" as used herein refers to the metals and metalloids of the aforementioned Groups of the Periodic Table.

One component of the catalyst system is one or more Lewis acids. Metal halides are preferred Lewis acids. Useful metal halide constituents include the fluorides, bromides and chlorides of titanium, vanadium, zirconium, niobium, tantalum, chromium, molybdenum, tungsten, arsenic, antimony, bismuth and the chlorides and bromides of gallium and aluminum. Group IVB, V and VIB metal fluorides are preferred metal halides, Group V being most preferred. Specific examples of useful metal fluorides include antimony pentafluoride, tantalum pentafluoride, niobium pentafluoride, vanadium pentafluoride, tungsten hexafluoride, titanium tetrafluoride, molybdenum and hexafluoride, bismuth pentafluoride, arsenic pentafluoride, mixtures thereof and the like. The fluorides, chlorides, and bromides of hosphorus, particularly phosphorus pentafluoride, are also suitable Lewis acids. The most preferred metal halide catalyst constituents are tantalum and niobium halides, preferably tantalum pentafluoride, niobium pentafluoride and mixtures thereof. Tantalum pentafluoride is meant to include the tantalum pentafluoride as well as other fluoride species, e.g., ions such as $Ta_2F_{11}^-$, $Ta_3F_{16}^-$ and the like, that may be formed when tantalum pentafluoride is mixed with the hydrogen halide. This applies similarly to other metal halides.

The second component of the catalyst system is a hydrogen halide. Useful hydrogen halides include hydrogen bromide, hydrogen chloride, and hydrogen fluoride. The preferred hydrogen halide catalyst constituent is hydrogen fluoride.

According to the present invention, applicants have found that the selectivity to $C_6$–$C_{12}$ branched alkylate is enhanced by use of a hydrogen halide, rather than other acids such as fluorosulfuric and trifluoromethanesulfonic, in combination with a metal halide. This is due primarily to minimizing the formation of intermediate esters, polymerization reactions and the like. While not wishing to be bound by any particular theory, applicants believe that such undesirable reactions are minimized because carboxylic acid ester formation does not occur in the presence of a hydrogen halide. As such, acid dilution and consumption due to concomitant self-alkylation, polymerization reactions, etc., i.e., reactions which lead to catalyst degradation, poorer product quality, and excess consumption of the hydrocarbon feedstock, are minimized. Another factor which is believed to contribute to the higher selectivity to $C_6$–$C_{12}$ branched alkylate with the present hydrogen halide containing acid systems is the lower solubility of the unsaturated organic materials, e.g. olefins, in the above-mentioned non-oxygenated acids.

It has also been discovered that the present alkylation process is more efficient when carried out in the substantial absence of aromatic compounds. In the present invention, the aromatic compounds will be readily alkylated to more basic compounds which in turn will dilute the acid catalyst and hence the effectiveness of the catalyst. Thus, although aromatic compounds may be present in the feedstock, it is preferred that the present alkylation process be conducted in their substantial absence, i.e. less than about 1 wt. %.

The effectiveness of the catalyst is related to the molar ratio of hydrogen halide to Lewis acid. While relatively minor amounts, i.e. less than equimolar amounts, of hydrogen halide relative to Lewis acid will dissolve at least a portion of the Lewis acid and thereby effect the reaction, the rate of reaction is inordinately slow. However, the reaction rate, i.e. the yield in a given period of time, will be increased if at least an equal molar amount of hydrogen halide relative to Lewis acid is present in the reaction zone. Increasing the mole ratio of hydrogen halide to Lewis acid provides additional hydrogen halide so as to dissolve more of the Lewis acid and thereby provide an increasing amount of liquid phase catalyst which will favor an increased reaction rate. The effect of increasing amounts of liquid phase catalyst on reaction rate becomes more pronounced when the mole ratio of hydrogen fluoride to Lewis acid is in excess of one and continues as the liquid phase of the catalyst increases. Thus, the mole ratio of hydrogen halide to Lewis acid (metal halide) is preferably at least 2:1 and more preferably at least 5:1. The favorable effects mentioned above will ultimately level off as the hydrogen halide dilutes the acidity of the reaction system. Thus depending upon the relative amounts of catalyst constituents used, the catalyst, when no support is employed, may be a homogeneous solution of the metal halide in the hydrogen halide or a mixture of solid and dissolved metal halide in hydrogen halide.

The amounts of the aforementioned catalyst present during alkylation is not critical to the practice of the present invention. In general, the catalyst is present in catalytic amounts. In the case of paraffin-olefin alkylation, at the point of olefin introduction, the olefin concentration on catalyst must be maintained at a low level, i.e. the amount of olefin introduced per unit time relative to the catalyst moving past the point of olefin introduction must be maintained at a low level. Therefore, the amount of olefin contacted with the catalyst can range from about 0.0001 to 0.05 parts by volume of olefin per part by volume of catalyst present in the reaction mixture. Preferably, the amount of olefin present will range from 0.0001 to 0.01 parts by volume per part by volume of the catalyst present.

In the case of paraffin-paraffin alkylation, the amount of larger paraffin contacted with the catalyst can range from about 0.1 to 10 parts by volume of paraffin per part by volume of catalyst present in the reaction mixture per hour. Preferably, the amount of larger paraffin present will range from 0.25 to 5.0 parts by volume per part by volume of catalyst present in the reaction mixture per hour. In addition, the volume percent of catalyst in the emulsion mixture; i.e., the liquid hydrocarbon plus catalyst, ranges from about 30 to about 85, preferably from about 50 to about 70.

The catalyst may be used as the neat liquid, as a diluted solution or as a solid, such as adsorbed on a solid support. If on a support, the catalyst may be used in a fluidized bed, in a molten salt process or suspended in a reaction mixture. With regard to the use of the catalyst in solution, any diluent or solvent may be used that is inert to the catalyst under the particular hydrocarbon conversion reaction conditions. To obtain optimum results, the diluents should be pretreated to remove catalyst poisons such as water and the like. Typical diluents or solvents include sulfuryl chloridefluoride, sulfuryl fluoride, sulfolanes, fluorinated hydrocarbons, Freons, polyfluorinatedpolyhalogenated hydrocarbons, mixtures thereof and the like. Hydrogen fluoride is the preferred catalyst diluent when the Lewis acid portion of the catalyst system is a metal fluoride. When a solvent or diluent is used, sufficient amounts are employed to maintain the viscosity of the catalyst mixture at a desired level. The amount of diluent employed can vary appreciably and can range as high as 98 volume % of the catalyst mixture. Preferably, the diluent:catalyst volume ratio may range from about 20:1 to 1:1. Higher dilutions may be desirable, for example, in those reactions that proceed with high exothermicity.

The catalyst may be mixed in the absence of any diluent. The components of the catalyst can be mixed separately, that is preferably in the absence of reactants, or in situ in the presence of reactants. In general, the order in which the reactants are added is not critical, thereby permitting a variety of procedures to be used.

The catalyst system may be incorporated with a suitable solid carrier or support. Any solid catalyst support may be used that is inert to the catalyst under the reaction conditions. If the support is not inert, the support should be pretreated, such as by heating, chemical treatment or coating, to remove substantially all water and/or hydroxylic sites that might be present. Reactive supports may be rendered inert by coating them with an inert material such as antimony trifluoride or aluminum trifluoride, or by treatment with Freons, fluorine or fluorinating agents such as when hydrogen fluoride is present in the catalyst. Suitable solid supports include fluoride-treated or coated resins such as sulfonated cation exchange resins, fluoride-treated acidic chalcites such as alumina and aluminosilicates and acid-resistant molecular sieves such as faujasite and zeolites, graphite, chromosorb T, Fluoropak 80, etc.

The supported catalyst can be prepared in any suitable manner, such as by conventional methods including dry mixing, coprecipitation or impregnation. In one embodiment, the supported catalyst is prepared by impregnating a suitable deactivated support with a Lewis acid such as tantalum pentafluoride and then with a hydrogen halide such as hydrogen fluoride. The weight ratio of the Lewis acid and hydrogen halide to the support can range from 1:100 to 1:10.

Olefins containing 2 to 8 carbon atoms per molecule are suitable for use in the present invention while olefins containing 2 and 6 carbon atoms per molecule are particularly preferred. The reaction mixture may also contain some amounts of diolefins. Although it is desirable from an economic viewpoint to use the normally gaseous olefins as reactants, normally liquid olefins may be used. The present invention also contemplates the use of polymers, copolymers, interpolymers, cross-polymers, etc., of the abovementioned olefins, as for example, the diisobutylene and triisobutylene polymers, the codimer of normal butylenes and the like. These materials are broken down into smaller units which can then be alkylated according to the process of the present invention. The use of mixtures of two or more of the above-described olefins is envisioned for use in the present process.

Paraffinic hydrocarbon feedstocks that are suitable for use in the present invention include the aliphatic and cycloaliphatic hydrocarbons. The aliphatic hydrocarbons (straight and branched chain materials) contain 4 to 12 carbon atoms per molecule ($iC_4-C_{12}$), preferably 4-8 carbon atoms ($iC_4-C_8$), and may be exemplified by isobutane, pentanes, hexanes, heptanes, and the like. The cycloaliphatic hydrocarbons (naphthenes) contain 5 to 15 carbon atoms per molecule, preferably 6 to 12 carbon atoms, and may be exemplified by methylcyclopentane, dimethylcyclopentane, ethylcyclohexane, n-pentylcyclohexane and the like.

It should be clearly understood that use of paraffinic hydrocarbon feedstocks having more than 12 carbon atoms per molecule, e.g., polymers, paraffinic waxes and the like, are contemplated in the present invention. However, such feedstocks will not be alkylated directly because paraffinic species having more than about 8 carbon atoms per molecule are less stable in a strong acid environment and will tend to break down to more stable, i.e. lower carbon number, reaction intermediates in the acid solution. The lower carbon number intermediates will then be alkylated according to the present invention to form desired liquid product. It is believed that cycloaliphatic hydrocarbons will behave in a similar manner but at a slower reaction rate.

The present invention is suitable for alkylating a paraffin with another paraffin. For example, a paraffinic feedstock containing smaller paraffins, i.e. isobutane, isopentanes, isohexanes or mixtures thereof, can undergo alkylation with larger paraffins, i.e. paraffins or a mixture of paraffins having more than 6 carbon atoms, to form lower molecular weight materials. Thus, isobutane can undergo a paraffin alkylation reaction with a heptane to form pentanes and hexanes, or with an octane to form essentially hexanes. Similarly, isopentane can be reacted with a heptane to form hexane products.

The present catalyst systems are particularly suited for use in refinery alkylation processes. The process of this invention contemplates the use of various refinery streams as feedstocks. Thus, $C_2$, $C_3$, $C_4$ and/or $C_5$ olefin cuts from thermal and/or catalytic cracking units; field butanes which have been subjected to prior isomerization and partial dehydrogenation treatment; refinery stabilizer bottoms; normally gaseous products from sulfuric acid or phosphoric acid catalyzed polymerization and copolymerization processes; and products, normally gaseous in character, from thermal and/or catalytic cracking units, are all excellent feedstocks for the present process. Such feeds are preferably dried to control excess water buildup, i.e. about 0.5 to 15 wppm, preferably about 0.5 to 2 wppm of water before entering the reactor.

In case of paraffin-olefin alkylation, the molar ratio of olefin to paraffin in the feed may range from 1:1 to 1:200, preferably from 1:3 to 1:50. In general, a high dilution of the olefin is preferred in order to prevent competitive side reactions such as olefin polymerization and self-alkylation reactions. In addition, the concentration of olefins dispersed in the acid should be low to allow substantially all of the olefin to be protonated. Thus, preferred operations are at low olefin feed rates relative to catalyst inventory; i.e., at low olefin space velocity. In the case of paraffin-paraffin alkylation, an excess of the smaller paraffin relative to the larger paraffin, should be maintained. Typically, the molar ratio of smaller paraffin to larger paraffin in the reaction zone should be in the range of from about 2:1 to about 100:1, preferably from about 3:1 to about 20:1.

It is necessary that the alkylation process of the present invention be conducted in the presence of hydrogen. The hydrogen serves as a moderator for cracking reactions that might occur and will hydrogenate free intermediates, polymeric materials as well as other unsaturated materials, which might be formed during the reaction and thus, be present in the acid phase. This also has the effect of increasing the life of the catalyst system.

The amount of hydrogen present in the acid catalyst during alkylation is not critical, provided there is an amount sufficient to saturate alkylation sludge precursors, i.e. to saturate the intermediate products formed during the break-up of any polymers formed during alkylation. Amounts ranging from about 0.1 to about 5.0 wt. % based on hydrocarbon feed are sufficient although greater amounts may be used. The hydrogen may be present in the form of a hydrogen-containing gas which may be obtained from any number of sources including commercially available pure hydrogen, naphtha reformers, hydrogen plants, as well as the off-gases from any hydrotreating process or hydrogen donor organic molecules such as tetralin, methylcyclohexane, decalin, isobutane and the like. The term "hydrotreating process" is meant to include hydrofining, hydrocracking, hydrodesulfurization and the like or synthetic schemes in which hydrogen is a product. The hydrogen-containing gas may be pure or contain other gaseous materials such as light hydrocarbons ($C_1-C_8$), carbon monoxide, carbon dioxide, hydrogen sulfide and the like. Depending upon the nature of the feedstock and the alkylation conditions, some of the $C_1-C_8$ light hydrocarbons will alkylate to form additional liquid product. The hydrogen-containing gas may be introduced into the alkylation process alone or be mixed with the hydrocarbon feed prior to said introduction. Preferably the hydrogen-containing gas will be dry.

The process catalyst system is somewhat sensitive to impurities such as water. Therefore, the present alkylation process should be conducted in the absence of large amounts of moisture, and preferably under substantially anhydrous conditions, i.e. less than 5 wt. %, preferably less than 2 wt. %, water, based on the Lewis acid component of the catalyst.

In general, the alkylation reaction temperatures will range from about −100° to about +100° C., preferably from about −30° to about +75° C., more preferably from about −10° to about +60° C. The pressure at which the reaction is carried out will depend upon the feedstream being processed, the reaction diluent, the hydrogen purity (i.e. less hydrogen present will require increased pressure) as well as other process variables. In general, the pressure should be sufficient to maintain at least a portion of one of the catalyst components in the liquid phase. Preferably the present alkylation process will be conducted substantially in the liquid phase when using an unsupported catalyst system. This may be expressed in terms of hydrogen partial pressure which should be at least 0.1 atmospheres and may range from about 0.1 to about 100 atmospheres, preferably from about 0.1 to about 50 atmospheres and most preferably from about 0.3 to about 25 atmospheres. The total pressure may range from about 0.1 to about 150 atmospheres. The present alkylation process may be conducted in the presence of an inert atmosphere such as nitrogen. It is preferred that said alkylation be conducted in the substantial absence of an oxygen-containing gas; i.e. less than about 1 wt percent oxygen based on the inert atmosphere.

In the present process, the reactants are contacted in the presence of a catalyst for a time sufficient to effect the degree of alkylation desired. In general, the contact time is subject to wide variation. The length of the contact time depends in part upon the temperature, the olefin used and the catalyst concentration employed. Typical contact times will range from about 0.05 seconds to several hours, preferably from about 0.05 seconds to about 1 hour, more preferably from about 0.05 seconds to about 45 minutes. The amount of catalyst employed for carrying out the present invention can vary appreciably such that, in general, the volumetric space velocity, based on the olefin, will range from about 0.01 to about 1 V/Hr/V, preferably from about 0.04 to about 0.2 V/Hr/V (volume of olefin per hour per volume of catalyst).

The alkylation process of the present invention may be conducted in a batch, intermittent or continuous operation. Preferably, the invention is carried out in a continuous manner to minimize further reaction of the product or products formed. It has been generally established that in alkylation processes, the more intimate the contact between the feedstock and the catalyst the better the yield of saturated product obtained. Thus, the apparatus employed may be of a conventional nature and comprise a single reactor or multiple reactors equipped with efficient stirring devices such as mechanical agitators, turbomixers, jet mixers and the like. One or more reactants may be introduced into the reaction zone through dispersion devices such as jets of restricted internal diameter, porous thimbles, and the like. The hydrocarbon paraffin-olefin or paraffin-paraffin phase, the catalyst phase and the hydrogencontaining gas may be passed through one or more reactors in concurrent, cross-current, or countercurrent flow. After a sufficient period of time, unreacted reactants, partially deactivated catalyst, inhibitors and heavier products of the reaction may be separated from the desired alkylation product and from one another, such as by distillation, and returned in whole or in part to the alkylation zone. If desired, a portion of the partially deactivated catalyst can be regenerated or reactivated by any suitable treatment and returned to the alkylation process.

As in other alkylation processes, more accurate control of the quality of the final product may be obtained if the reaction system is provided with a recycling feature wherein the partially converted hydrocarbons are mixed with fresh feed and returned to the feed dispersion device in the reaction zone. However, due to the high conversion efficiency of the present catalyst systems, it is preferred to effect alkylation in a once-through operation with short contact times.

Reactions involving the use of the present catalyst systems can be conducted in vessels fabricated from carbon steel provided that excessive temperatures are not used and provided further that the reaction system is maintained in a substantially anhydrous condition. Teflon, Carpenter 20 Cb-3 (Alloy 20) steel or Monel may also be used in the fabrication of reaction equipment as well as aluminum-magnesium alloys, e.g., aluminum 5052 and the like.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944; 2,479,366; 2,701,184; 2,717,913; 2,775,636; 3,766,293; U.K. Pat. Nos. 543,046; 577,869; 731,806; 738,348; U.S. Pat. No. 803,458; U.K. Pat. Nos. 804,966, and 881,892, the disclosures of which are incorporated herein by reference.

Use of the present invention results in the production of an alkylate having more highly branched isomers that have a higher octane number than the hydrocarbon feedstocks. As such the alkylate product is particularly well suited for use as blending components for a refinery motor gasoline pool.

The following examples are presented to further illustrate the process of the present invention and are not intended to unduly restrict the limits of the claims appended hereto;

EXAMPLE 1

Into a 300 ml Hastelloy C Autoclave Engineer's stirred autoclave were placed tantalum pentafluoride (27.6 g, 0.10 mole), hydrogen fluoride (2.8 g, 0.15 mole) and isobutane (52.2 g, 0.90 mole). The reaction mixture was heated to 40° C. Ethylene (2.8 g, 0.1 mole) at 140 psi and hydrogen (0.07 mole) at 100 psi were added to the reaction mixture which was being stirred at about 1600 rpm. Cold water was circulated through an internal cooling coil to help the thermostat maintain a temperature of 40° C while the ethylene, which reacts very exothermically, was added. Any temperature rise would result in loss of ethylene via polymerization, a phenomenon which is also counterbalanced by the presence of both excess hydrogen fluoride and hydrogen. A sample was taken at 40° C by connection of an evacuated 10 ml stainless steel cylinder to the reactor. When the valves connecting the two vessels were opened, product passed from the reactor through the dip stick into the smaller vessel by the difference in pressure. The sample was cooled to −70° C and an aliquot of the vaporized liquid was analyzed on a Perkin Elmer 900 Gas Chromotograph with a flame ionization detector using a DC-200 capillary column at 50° C. The results indicate the following product distribution excluding reactants:

| Product Distribution | % |
|---|---|
| $C_2$ | Trace |
| $C_3$ | 7.3 |
| n-$C_4$ | — |
| i-$C_5$ | 7.3 |
| n-$C_5$ | 1.8 |
| Hexanes | 83.6 |
| 2,2-$DMC_4$ | Trace |
| 2,3-$DMC_4$ | 67.4 |
| 2-MP | 23.9 |
| 3-MP | 8.7 |

Example 1 shows that for paraffin-olefin alkylation the present catalyst system is highly selective to the formation of hexane, e.g. about 83.6% of the product excluding reactants are hexanes, and to the branched, higher octane components in the hexanes, e.g. about 67% of the hexane product is 2,3-dimethylbutane.

EXAMPLE 2

Into a 300 ml Hastelloy C Autoclave Engineer's stirred autoclave were placed tantalum pentafluoride (55.2 g, 0.20 mole), hydrogen fluoride (40.0 g, 2.0 mole), isobutane (116 g, 2.0 mole), n-heptane (40 g, 0.4 mole) and hydrogen (~5 psi, 0.004 mole). The reaction mixture was stirred at 1000 rpm and heated to 40° C. After about 30 minutes of reaction at 40° C., a sample was collected and analyzed as in Example 1 to give the following results, excluding reactants:

| Product Distribution | % |
|---|---|
| $C_5$ | 63.7 |
| $C_6$ | 29.10 |
| $C_7$ | 7.2 |
| i-$C_5$ in $C_5$'s | 82.7 |
| 2,2-$DMC_4$ in $C_6$'s | 52.4 |

Example 2 shows that the present catalyst system is also highly active and selective to the formation of desirable high octane branched isomers via paraffin-paraffin alkylation.

What is claimed is:

1. An alkylation process wherein i-$C_4$–$C_{12}$ aliphatic hydrocarbons are alkylated with olefins under substantially anhydrous alkylation conditions and in the presence of hydrogen and of a catalyst comprising (a) a metal fluoride selected from the group consisting of tantalum pentafluoride, niobium pentafluoride and mixtures thereof, and (b) hydrogen fluoride, and forming an alkylate product having an octane number greater than that of the feedstock.

2. The process of claim 1 wherein the ratio of hydrogen fluoride to metal fluoride is at least equimolar.

3. The process of claim 1 wherein said alkylation occurs in the substantial absence of aromatic compounds.

4. The process of claim 1 wherein sufficient hydrogen is present to maintain a hydrogen partial pressure of at least 0.1 atmosphere.

5. The process of claim 1 wherein said alkylation occurs substantially in the liquid phase.

6. The process of claim 1 wherein said olefin is a $C_2$ – $C_8$ olefin.

7. The process of claim 1 wherein the molar ratio of olefin to paraffin in the feed ranges from 1:1 to to 1:200.

8. The process of claim 1 wherein said catalyst is supported on a solid carrier that is substantially inert to the supported acid.

9. An alkylation process which comprises alkylating i-$C_4$–$C_8$ aliphatic hydrocarbons with $C_2$ to $C_8$ olefins in an alkylation zone under substantially anhydrous conditions in the presence of hydrogen and of a catalyst comprising (a) a metal fluoride selected from the group consisting of tantalum pentafluoride, niobium pentafluoride and mixtures thereof and (b) hydrogen fluoride, wherein the ratio of hydrogen fluoride to metal fluoride is at least equimolar, said alkylation taking place substantially in the liquid phase, at a temperature ranging from about −30° to about +75° C, a hydrogen partial pressure ranging from about 0.1 to about 50 atmospheres, and forming an alkylate product having an octane number greater than that of the feedstock.

10. The process of claim 9 wherein the molar ratio of olefin to paraffin in the feed ranges from 1:3 to 1:50.

11. The process of claim 9 wherein said olefins contain 2–6 carbon atoms per molecule.

12. The process of claim 9 wherein the molar ratio of hydrogen fluoride to metal fluoride is at least 2:1.

13. The process of claim 9 wherein a polymeric material derived from an olefin is present in said alkylation zone.

14. The process of claim 9 wherein said alkylation is conducted in the substantial absence of aromatic compounds.

15. The process of claim 9 wherein the hydrogen partial pressure ranges from about 0.3 to about 25 atmospheres.

* * * * *